United States Patent [19]

Pigmans

[11] Patent Number: 4,590,940
[45] Date of Patent: May 27, 1986

[54] SUN BED WITH IMPROVED RADIANT PERFORMANCES

[76] Inventor: Wilhelmus A. M. Pigmans, Koeistratt, 1, Arendonk, Belgium

[21] Appl. No.: 618,162

[22] Filed: Jun. 7, 1984

[30] Foreign Application Priority Data

Jun. 7, 1983 [BE] Belgium .............................. 2/60123

[51] Int. Cl.⁴ ............................................. A61N 5/06
[52] U.S. Cl. .................................... 128/376; 128/396; 250/455.1
[58] Field of Search ............... 128/395, 396, 372, 373, 128/376; 250/453.1, 454.1, 455.1

[56] References Cited

U.S. PATENT DOCUMENTS 4,335,724 6/1982 Frei et al. ............................ 128/395

FOREIGN PATENT DOCUMENTS 3005487 8/1981 Fed. Rep. of Germany ...... 128/396

OTHER PUBLICATIONS

Suntana Sun System brochure, 2 pages.

*Primary Examiner*—Anton O. Oechsle
*Attorney, Agent, or Firm*—Cushman, Darby & Cushman

[57] ABSTRACT

The invention relates to a sun bed equipped in the lengthwise direction with tube lamps, which sun bed is carried out in the shape of a tunnel.

3 Claims, 1 Drawing Figure

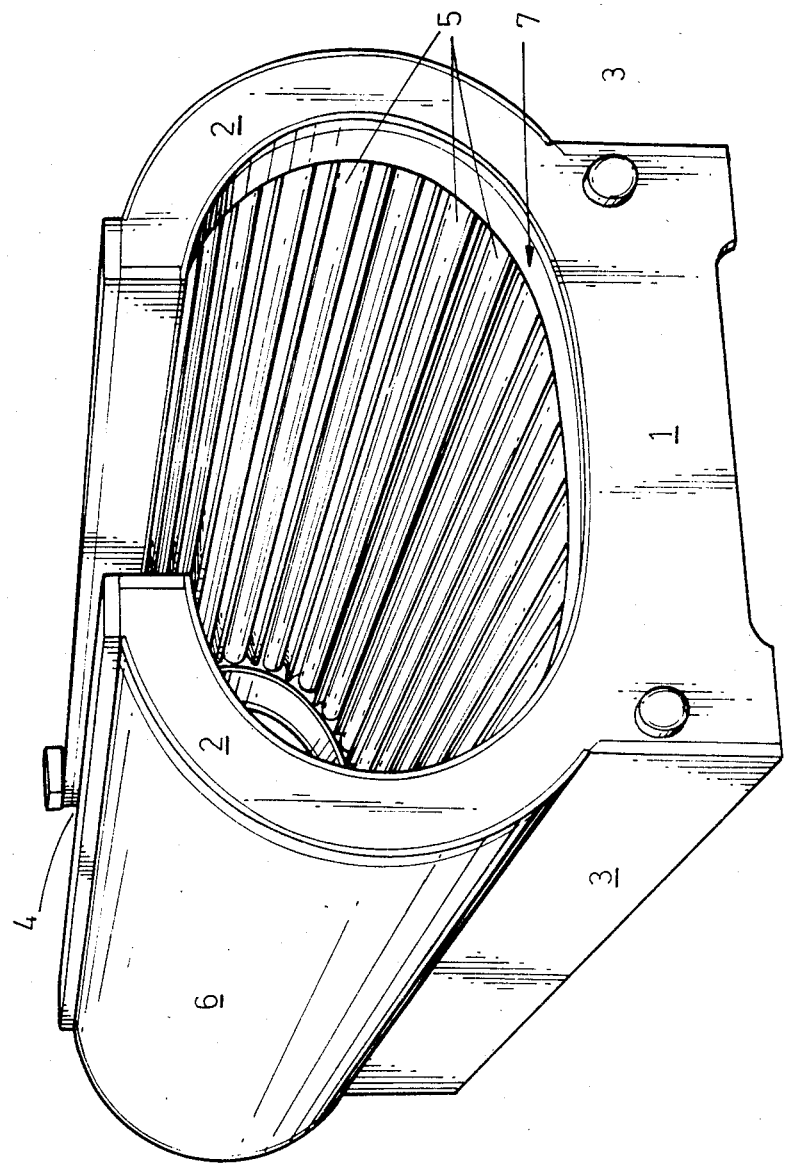

SUN BED WITH IMPROVED RADIANT PERFORMANCES

This invention concerns a novel and original sun bed which offers an optimum use of the light sources consisting of tube lamps and a greater comfort to the user.

Sunbed equipments with lower light sources arranged in a horizontal or nearly horizontal plane in a base unit are well known. Generally, a top unit also equipped with tube lamps is arranged above the base unit to combine the effects of the upper and lower light sources. Mounting such a top unit or ceiling needs an important structure if the top unit is not connected hingedly to the base unit.

The invention has for an object to overcome the drawbacks of present well known sun beds and to realize a sun bed with widely improved radiant performances.

To this end the sun bed according to the invention is carried out in the shape of a tunnel.

Still according to the invention said sun bed is fitted out internally with a sheet of synthetic transparent material which constitutes a support for the user and a protection for the tube lamps.

Other details and advantages of the invention will result from the specification of a sun bed according to the invention which is given by way of an example and will not limit the scope of the invention. The specification refers to the accompanying drawing.

The drawing is a perspective view of the sun bed according to the invention.

The sun bed shown by the drawing comprises a frame made of a base plate 1 which extends into two curved arms 2 which determine the transverse profile of the sun bed. In the lengthwise direction of the sun bed the base of the frame consists of two plates 3.

At the upper part of the sun bed a longitudinal slot 4 is provided which allows the user to have access to the inner of the sun bed. The thermal equipment of the sun bed consists of tube lamps 5 arranged between an insulating envelop 6 and a transparent sheet 7 of synthetic material. This sheet 7 which is adapted to the elliptic shape of the transverse section of the sun bed can be made of any appropriate synthetic material, e.g. an acrylic resin.

The maximum width of the sun bed is such that the radiations emitted by the tube lamps reach the users in the best possible conditions.

The curvature of the sheet 7 procures a better support to the users body. This is not the case when the sun bed has a base unit equiped with a plane or nearly plane sheet which offers no comfort to the user.

The radiations concentrate better, as a result of the elliptic section of the tunnel shaped sun bed so the user's body is fully and regularly irradiated without moving from its resting position.

I claim:

1. A sun bed comprising:
   a fixed frame defining an open-ended tunnel-shaped horizontal enclosure, generally eliptical in cross-section, having a generally horizontal major dimension;
   means defining a longitudinal slot in the top of said enclosure extending the entire length thereof and of a width sufficient to provide access therethrough for a user of said bed; and
   rows of tanning tube lamps secured to the inner sides of said enclosure and extending lengthwise thereof.

2. The sun bed defined in claim 1 including heat insulation between said lamps and the outer sides of the enclosure.

3. The sun bed defined in claim 1 including transparent sheet material lining the interior of the enclosure to protect the lamps and provide a support for a user of said bed.

* * * * *